(12) United States Patent
Fox

(10) Patent No.: US 7,504,262 B2
(45) Date of Patent: Mar. 17, 2009

(54) HIGH SENSITIVITY BIOMOLECULE DETECTION WITH MAGNETIC PARTICLES

(76) Inventor: John Fox, 10951 Sorrento Valley Suite 2G, San Diego, CA (US) 92121-1613

( * ) Notice: Subject to any disclaimer, the term of this patent is extended or adjusted under 35 U.S.C. 154(b) by 0 days.

(21) Appl. No.: 11/361,828

(22) Filed: Feb. 23, 2006

(65) Prior Publication Data

US 2007/0207553 A1 Sep. 6, 2007

(51) Int. Cl.
*G01N 25/18* (2006.01)
(52) U.S. Cl. ............... 436/149; 436/526; 436/528; 436/151; 324/200; 324/222; 324/223
(58) Field of Classification Search ............ 436/149, 436/526, 528, 151; 324/200, 222, 223
See application file for complete search history.

(56) References Cited

U.S. PATENT DOCUMENTS 5,470,534 A * 11/1995 Imai et al. ............... 422/67
5,506,098 A * 4/1996 Zarling et al. ............ 435/6

OTHER PUBLICATIONS

Baselt et al. (Biosensor & Bioelectronics 1998 vol. 13, p. 731-739).*

* cited by examiner

*Primary Examiner*—Mark L Shibuya
*Assistant Examiner*—Jacob Cheu

(57) ABSTRACT

The present invention generally relates to the field of biomolecule detection. More specifically, the present invention relates to compositions, methods and systems for the detection and manipulation of biomolecules using magnetic particles.

33 Claims, 4 Drawing Sheets

HIGH SENSITIVITY BIOMOLECULE DETECTION WITH MAGNETIC PARTICLES

CROSS-REFERENCE TO RELATED APPLICATION

This application claims priority based on U.S. provisional patent application No. 60/150,210 filed Aug. 21, 1999, which is hereby incorporated by reference in its entirety.

FIELD OF THE INVENTION

The present invention generally relates to the field of biomolecule detection. More specifically, the present invention relates to compositions, methods, and systems for the detection and manipulation of biomolecules using magnetic particles.

BACKGROUND OF THE INVENTION

In basic research, one goal is to understand how genes are distributed within populations and how expression of those genes leads to phenotypic differences. This information has the potential to become a powerful tool for predicting human health trends and has been a driving force behind the search for genetic markers for human disease.

Over the years, many biochemical techniques have been introduced for analyzing the presence and/or amount of a biomolecule in a sample. As examples, a number of organic stains have been adapted for the detection of electrophoretically separated proteins, including Bromphenol Blue, Coomassie Blue, Fast Green (Food Green 3) and Amido Black (Acid Black 1). (See Durrem, *J. Am. Chem. Soc.* 72:2943 (1950), Grassman and Hannig, *Z. Physiol. Chem.* 290:1 (1952), Fazekas De St. Groth et al., *Biochim. Biophys. Acta* 71:377 (1963), and Meyer and Lamberts, *Biochim. Biophys. Acta* 107:144 (1965)). Fluorescent stains, such as fluorescamine and 2-methoxy-2,4-diphenyl-3(2H)-Furanone (MDPH), are also used to detect proteins (See Ragland et al., *Anal. Biochem.* 59:24 (1974) and Pace et al., *Biochem. Biophys. Res. Commun.* 57:482 (1974)). A sensitive technique for staining proteins is silver staining. (See Merril et al., *Proc. Natl. Acad. Sci. USA* 76:4335 (1979) and Switzer et al., *Anal. Biochem.* 98:231 (1979)). While these techniques may be useful to resolve total protein in a sample, they are limited in their usefulness to detect a specific protein in a heterogeneous population of proteins.

The detection of specific proteins in a sample can be accomplished by techniques including Western blot, immunoprecipitation, enzyme-linked immunoassay (ELISA), and sandwich assays. These techniques typically use radioactivity, fluorescence, and chemiluminescence to label or mark an antibody or other protein which binds to the target protein and thereby identifies the presence and/or location of the target. Depending on the quality of the antibody and the label used, the sensitivity of detection and non-specific binding varies.

Radioactivity, fluorescence, and chemiluminescence are also commonly used for the detection of specific nucleic acid sequences in a sample. Hybridization techniques, such as Southern and Northern blotting, are frequently employed to detect the presence of polymorphisms in a nucleic acid sample. In nucleic acid hybridization, for example, a radioactive label (e.g. $^{32}$P or $^{35}$S) is incorporated into an oligonucleotide probe which complements a target nucleic acid, and hybridization with the target is accomplished at a specific salt concentration and temperature. (See e.g. Sambrook, J. et al., *Molecular Cloning, A Laboratory Manual* (1989)).

Southern et al. has used nucleic acid hybridization by setting up an array of oligonucleotides on plastic and glass, probing with a radioactive oligonucleotide, and detecting the presence of a target nucleic acid with a PhosphorImager. (See Southern, E. M. et al., *Nucleic Acids Res* 22, 1368-1373 (1994)). The PhosphorImager instrument, an expensive laser based optical system, and clean image-ready phosphor screens are needed for each sample read, making the system both cumbersome and very expensive. In addition, radioactive probes have a short shelf life ($T_2$=days to months) and require tight inventory control in a licensed facility. Although some companies are currently performing genetic screening using this method, the cost is prohibitive for most diagnostic procedures.

Others in the field are pursuing methods more predisposed to automation in hopes of enabling the rapid screening of a sample for a number of sequences. As one example, Affymetrix (Santa Clara, Calif.) has described a system which performs on-chip hybridization. (See Kreiner, T., *American Laboratory* March:39-43 (1996). In this system, oligonucleotides are arrayed in 90×90:m cells with $10^7$ oligonucleotides per cell, with 20,000 probe cells on each chip. This is annealed with fluorescence-labeled probes, and detection is carried out using a 488 nm Argon laser (8:m shot size) as a excitation source and a photomultiplier tube to detect the fluorescence emission. To read the chip, an optical system consisting of a dichromic mirror, scanning head, routing mirror and a confocal optical system are employed. One significant problem with this approach is non-specific background. Several natural occurring molecules either contribute to or quench the fluorescent signal, making this technique prone to a background noise which prevents this system from achieving highly sensitive nucleic acid detection.

Chemiluminescence is another marker employed to detect biomolecules. Chemiluminescence uses an enzyme coupled to the probe which catabolizes a chemical substrate to generate a photon. (See Bronstein, et al., *BioTechniques* 8:310-313 (1990)). Chemiluminescence nucleic acid hybridization assays may use a high performance, low-light-sensitive charge coupled device (CCD) camera to image the light emission from the chemical reaction. Often the camera is controlled by a personal computer and the images are archived on diskettes. While the CCD cameras are robust, CCD based systems do not have the sensitivity of film and the reagents have a one-year shelf life when stored at 4° C. (Tropix Inc.). As with fluorescence detection approaches, this approach is limited by background noise caused by naturally occurring enzymes or compounds contributing to the signal.

As the secrets of genomic regulation and the biosynthesis of enzymes, receptors, and ligands involved in human disease unfold, the need for detection techniques which provide a high degree of specificity and sensitivity with minimal background noise, while minimizing cost and handling issues, is manifest. In view of the foregoing, and notwithstanding the various efforts exemplified in the prior art, there remains a need for novel compositions, methods, and systems for highly sensitive biomolecule detection.

SUMMARY OF THE INVENTION

Recognizing the limitations associated with current techniques for detection, manipulation and separation of biomolecules, the present invention provides methods and systems for the detection and manipulation of biomolecules using magnetic particles. Through its embodiments, the present invention improves specificity and sensitivity while minimizing background, cost and handling issues related to biomolecule detection and manipulation.

The present invention includes highly sensitive biomolecule detection methods and systems which use a magnetic moiety as a marker to determine the presence and/or location of a specific target biomolecule, The invention detects target molecules or molecular biomolecules that have been contacted directly or indirectly with a magnetically labeled probe by subjecting the target-probe complex to an applied magnetic field and determining the resulting magnetic characteristics. The invention provides methods and systems to prepare such magnetic probes and to identify the presence and/or location of the target biomolecules disposed on a support or in solution. The invention may detect characteristic responses of samples by several means, including but not limited to, by induced magnetization or orientation changes of magnetically labeled biomolecules.

The present invention also provides methods and systems for nucleic acid hybridization using magnetic labels, ferrofluids, and nonmagnetic colloids, as some examples.

The present invention also provides methods and systems to study competitive binding and also provides methods and systems which use magnetic labels to screen for, manipulate, and separate target biomolecules, for example, in the same sample.

Methods and systems for the detection and separation of nucleic acids, as one example only, using ferrofluids and beads, are also provided. The invention also includes methods and systems to enhance the binding of a probe to a target biomolecule and methods to reduce the background noise in hybridizations and binding assays.

DETAILED DESCRIPTION OF THE PREFERRED EMBODIMENTS

Figure 1:
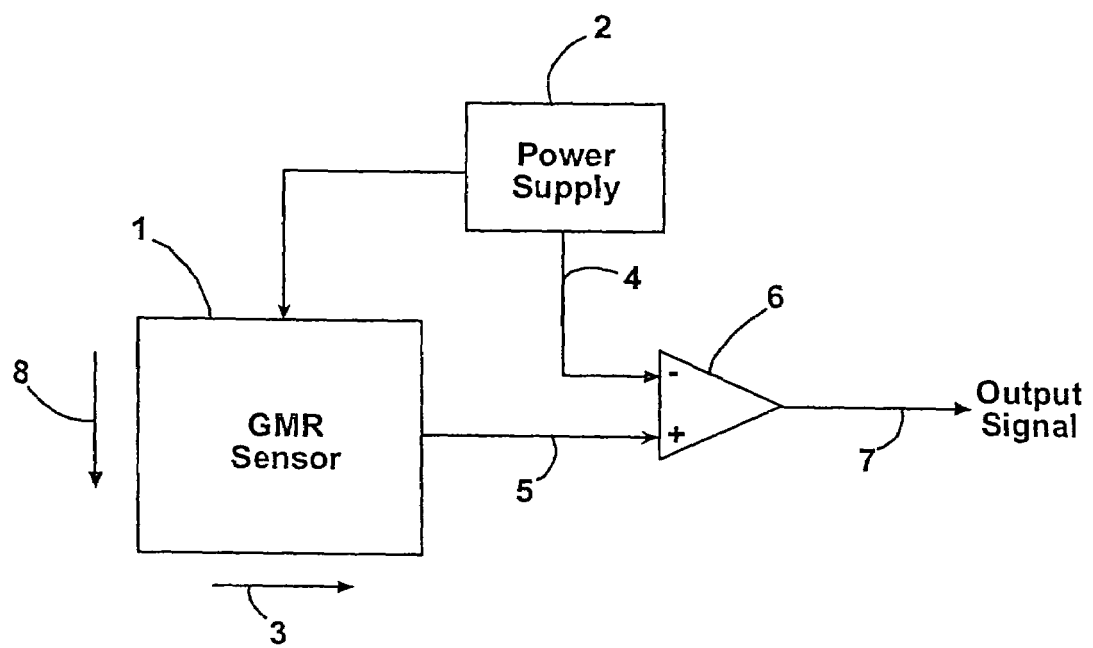
FIG. 1 displays a block diagram of an embodiment of a magnetic detection apparatus used to detect a magnetic particle joined to a biomolecule.

The present invention comprises highly sensitive biomolecule detection methods and systems which use a magnetic moiety as a marker to determine the presence, location, and/or quantity of a specific target biomolecule, by way of examples only, a protein, lipid, or a nucleic acid, in a sample. Many types of magnetic labels may be joined to biomolecules in embodiments of the present invention. As examples only, preferred magnetic labels may include $Fe^3O^4$, $Fe^2O^3$, and rare-earth elements with atomic numbers between 64 and 69, inclusive, which have been incorporated into a colloidal suspension. In some preferred embodiments the magnetic labels are attached directly to the biomolecule, as one example only, a ferrofluid bound to a nucleic acid or protein, or in other embodiments, the magnetic label is indirectly attached to the biomolecule, e.g., through an intermediate, such as an antibody, a binding protein (e.g., avidin, streptavidin, and derivatives thereof), or a chemical linker.

Although attachment of a magnetic label, such as a ferrofluid, to a biomolecule disposed on a support is used in some embodiments of the present invention for the rapid identification of the presence, location, or quantity of a biomolecule, magnetically labeled biomolecules are also used as magnetic probes to specifically identify a target biomolecule which may be present in a heterogeneous sample of biomolecules. Accordingly, the invention provides methods and systems to prepare such magnetic probes and to identify the presence and/or location of the target biomolecules disposed on a support. One skilled in the art will appreciate that conventional approaches to nucleic acid hybridization and protein identification (e.g., immunoblotting and ELISA) are readily adapted to the magnetic detection methods and systems disclosed in preferred embodiments of the present invention. Furthermore, the present invention provides methods and systems to study competitive binding and techniques which enable the screening for several target biomolecules in the same sample.

In one embodiment, the present invention detects magnetically labeled biomolecules by measuring or characterizing the magnetic signal generated by the magnetic particle joined to the biomolecule. In several preferred embodiments, the invention uses a sensitive magnetic sensor, such as a giant magnetoresistive ratio sensor (GMR), for the detection of magnetically labeled biomolecules. A method of biomolecule detection according to one preferred embodiment of the present invention is as follows: A biomolecule is disposed on a support. Then the biomolecule is bound with a magnetic label which generates a magnetic signal, or the biomolecule is bound with a magnetically-labeled probe which generates a magnetic signal. The unbound magnetic label or unbound magnetically-labeled probe is removed by washing. Subsequently, the support having the biomolecule and attached magnetic label or biomolecule-magnetic probe complex is passed before a magnetic sensor which detects the presence and location of the magnetic probes and their specific magnetic characteristics. By characterizing the properties of a magnetically labeled biomolecule in an applied magnetic field, as one example only, by defining the hysteresis loop, solving one or more of the parameters of the hysteresis loop (e.g., saturation magnetization, remnant magnetization, and coercive force) or both, the identity as well as the quantity and location of the magnetic label are determined.

Additionally, the invention comprises methods and systems for the detection of one or more different biomolecules in the same sample by using magnetically labeled probes having different magnetic particles. Because many different magnetic particles exist and each has a unique magnetic signature, the detection of several different magnetically labeled biomolecules in the same sample is accomplished. Notably, the size and geometry of the magnetic particle affect magnetic characteristics, and therefore magnetic labels with homogeneous magnetic particles are preferred.

Further, the invention comprises methods and systems which permit the rapid screening for the presence of one or more target biomolecules in a solution. In one embodiment, one or more colored beads joined to a probe biomolecule, as examples only, an antibody or an oligonucleotide, are used to detect magnetically labeled target biomolecules in a solution. In additional embodiments, one or more different colored beads are joined to one or more different probe biomolecules so as to detect the presence and amount of several different target biomolecules in the same sample solution. Accordingly, the invention comprises methods by which colored beads having one or more probe biomolecules are bound to magnetically labeled target biomolecules, and a magnetic field is applied so as to separate colored bead-probe-target complexes from colored beads having probe biomolecules which have not bound to magnetically labeled target biomolecules. The presence and amount of target biomolecules in the sample is then determined by the efficiency at which the colored beads respond to the applied magnetic field, as detected visually or with the aid of electronic and/or optical devices, such as a spectrophotometer or a photodiode CCD camera.

Additional embodiments may include, as examples only, fluorescent beads or fluorescent cells which produce fluorescent signals (for example, like green fluorescent protein), with subsequent measurement of fluorescence.

In additional embodiments, the presence of a target biomolecule in a sample solution is determined by monitoring the time it takes for a magnetic particle to reorient itself in response to a repositioning of an applied magnetic field ("magnetic swing time"). Because magnetically labeled probes attached to target biomolecules, for example, reorient their alignment to a shifted magnetic field more slowly than unattached magnetically labeled probes, the presence of a target biomolecule in a sample solution is easily determined. Preferably, embodiments that detect the presence of a target biomolecule in a sample solution by "magnetic swing time" have magnetically labeled probes attached to beads that exhibit a strong polarization orientation in a magnetic field or magnetically labeled probes that have magnetic particles that are needle-like.

The invention also comprises methods and systems to enhance the binding of a probe to a target biomolecule and methods to reduce the background noise in hybridizations and binding assays. By applying a magnetic or electric field, or both, to regions of a support where a target biomolecule is disposed, for example, the movement toward and concentration of a magnetically labeled probe biomolecule near the region of the support having the target biomolecule is obtained. Advantages include improved binding kinetics and conservation of probe materials. Alternatively, a magnetic or electrical field, or both, is applied after a target biomolecule is bound by the magnetically labeled probe biomolecule so as to remove or separate from the target biomolecule and support any unbound or non-specifically bound magnetically labeled probe biomolecules. Further, the invention provides methods and systems by which ferrofluid-labeled biomolecules are efficiently separated according to their magnetic potential, and in which ferrofluid-labeled biomolecules in a solution are separated in an applied magnetic field. Because the amount of ferrofluid bound to the biomolecule is directly related to the mass of the biomolecule, the invention comprises a magnetic-mass based separation technique in one embodiment.

Some preferred embodiments use types of magnetic labels. A "magnetic label" or "magnetic marker" is any transiently or permanently magnetized entity. In some embodiments of the present invention, a magnetic label comprises a magnetic particle that is ferromagnetic or ferrimagnetic or paramagnetic or superparamagnetic. The magnetic markers or labels preferably generate a magnetic signal, which can be, by way of example only, the magnetic field generated by ferromagnetic and ferrimagnetic materials, or the attraction for magnets characteristic of paramagnetic and superparamagnetic materials. In solution, the magnetic moments of the particles desirably align with each other.

In some embodiments, a magnetic label comprises a plurality of colloidal iron particles that define a respective magnetic moment. The term "magnetic labels" also refers to magnetic particles which comprise metal, metal compounds, or nuclei coated with a metal or metal compound. In some embodiments, preferable magnetic labels include ferrofluids or other magnetizable colloids. Additionally, the term "magnetic label" refers to a magnetic particle including iron, cobalt, nickel, ferrous oxide, ferrous hydroxide, and other ferrous alloys, disposium oxide, and rare earth elements with atomic numbers between 64 and 69, inclusive, or magnetite ($Fe_3O_4$), maghemite ($Fe_2O_3$), and other mixed oxides. Magnetic labels having rare-earth magnetic particles are desirable because they may have a five-fold greater magnetization than iron oxide beads. The term "magnetic label" also refers to the magnets discussed in Vassiliou et al., *J. Appl. Physics* 73(10); 5109 (1993)), the disclosure of which is hereby incorporated by reference in its entirety.

One of ordinary skill in the art will appreciate that there are available biomolecule separation techniques that can be used prior to disposing a desired biomolecule on a support or used to separate and dispose the biomolecule on a support. There may be advantages for separating the desired biomolecule from other biomolecules present in a sample prior to contacting the sample with a magnetic label or a magnetically labeled probe biomolecule. Notably, the separation of the desired biomolecule often facilitates the isolation of the biomolecule after identification. The separation of the desired biomolecule from others in the sample is not necessary, however, to practice preferred embodiments of the present invention.

The present invention includes several methods and systems by which a target biomolecule can be disposed on a support in preparation for detection with magnetic labels or magnetically labeled probe biomolecules.

The separation of biomolecules prior to detection is accomplished, for example, by a one-dimensional or two-dimensional electrophoresis procedure. (See e.g., *Methods in Enzymology* Vol. 182, Guide to Protein Purification, ed. Deutscher, Academic Press Inc. pp. 425-477, San Diego, Calif. (1990), *Current Protocols in Molecular Biology*, Ausubel et al., ed., John Wiley & Sons (1994-1998), and Sambrook et al., *Molecular Cloning: A Laboratory Manual.* 2 ed., Cold Spring Harbor Laboratory, Cold Spring Harbor, N.Y. (1989)). Denaturing and non-denaturing gel electrophoresis are frequently used to separate nucleic acids, and sodium dodecyl sulfate polyacrylamide gel electrophoresis (SDS/PAGE) is a common method to separate proteins. Further, pulse-field electrophoresis, two-dimensional protein electrophoresis, isoelectric focussing, and other separation techniques are used to separate target biomolecules prior to detection with a magnetic label or a magnetically labeled probe. Additionally, biomolecules can be separated chromatographically, for example, by thin layer chromatography (TLC), by liquid chromatography techniques, such as high performance liquid chromatography (HPLC) or fast performance liquid chromatography (FPLC), or by affinity chromatography techniques, prior to detection with a magnetic label or a magnetically labeled probe.

Another common laboratory technique called "blotting" is also used to dispose a target biomolecule on a support. This technique allows for the transfer of separated biomolecules on a matrix to a solid membrane or a filter. (See e.g., *Current Protocols in Molecular Biology*, Ausubel et al., ed., John Wiley & Sons (1994-1998), and Sambrook et al., *Molecular Cloning: A Laboratory Manual.* 2 ed., Cold Spring Harbor Laboratory, Cold Spring Harbor, N.Y. (1989)). Additionally, biomolecules disposed on a membrane support by blotting are frequently immobilized or fixed into position so that further rounds of detection can be accomplished. By "stripping" or removing the first bound probe by techniques known in the art, subsequent rounds of detection with new magnetically labeled probes are performed.

In preferred embodiments, the present invention may include a "matrix" or "support" which may be a carrier, a bead, a resin, or any macromolecular structure used to attach, join, immobilize, or dispose thereon a biomolecule, by way of examples only, a nucleic acid, lipid, or protein. Supports may include, but are not limited to, the walls of wells of a reaction tray, test tubes, polystyrene beads, fluorescent beads, magnetic beads, nitrocellulose strips, membranes, microparticles such as latex particles, sheep (or other animal) red blood cells, cells, fluorescent particles, duracytes® and others. Additionally, organic carriers including proteins and oligo/polysaccarides (e.g. cellulose, starch, glycogen, chitosane or aminated sepharose) and inorganic carriers such as silicon oxide material (e.g. silica gel, zeolite, diatomaceous earth or aminated glass) may be used in embodiments of the present invention. Furthermore, in some embodiments, a liposome or lipid bilayer (natural or synthetic) may be used as a support. Desirable supports may also include polyacrylamide gels, agarose gels, composite gels, and other gel matrices, papers, chips, membranes, chromatography matrices, as used in thin layer chromatography, and resins or beads, as used in affinity chromatography.

In some embodiments of the present invention, the support has a hydrophobic surface that interacts with a portion of the biomolecule by hydrophobic non-covalent interaction. As one example only, the hydrophobic surface of the support is oftentimes a polymer such as plastic or any other polymer in which hydrophobic groups have been linked, such as polystyrene, polyethylene or polyvinyl. In some embodiments, the support has a charged surface which interacts with the biomolecule, as one example only, a charged nitrocellulose or nylon membrane. In other embodiments, the support is attached to a biomolecule through a linker, such as biotin-avidin or biotin-streptavidin, or biotin and an-avidin or streptavidin derivative. The supports used in some embodiments of the present invention have other reactive groups which are chemically activated so as to attach a biomolecule. As some examples, cyanogen bromide activated matrices, epoxy activated matrices, thio and thiopropyl gels, nitrophenyl chloroformate and N-hydroxy succinimide chlorformate linkages, and oxirane acrylic supports art are adapted for use in some embodiments.

In the present invention, any type of biomolecule, by way of examples only, proteins, polypeptides, nucleic acids, and lipids, can be joined or disposed on a support and subsequently joined to a magnetic label. Further, preparations of biological samples having biomolecules can be joined or disposed on a support. In preferred embodiments, several different biomolecules or different preparations of biological samples having biomolecules are attached to a support in an ordered array wherein each biomolecule or preparation of biological sample is attached to a distinct region of the support which does not overlap with the attachment site of any other biomolecule or preparation of biological sample. Preferably, such an ordered array is designed to be "addressable" where the distinct locations are recorded and can be accessed as part of an assay procedure.

In some embodiments, addressable biomolecule arrays comprise a plurality of different biomolecule probes that are joined to a support in different known locations. The knowledge of the precise location of each biomolecule probe makes these "addressable" arrays particularly useful in binding assays. As one example only, an addressable array can comprise a support joined to many different antibodies that recognize different human proteins that are tumor markers for various forms of cancer. The proteins from a preparation of biological sample from a human subject are magnetically labeled (e.g., using a ferrofluid labeling process, discussed below), and the magnetically labeled sample is applied to the array under conditions that permit antibody binding. If a protein in the sample is recognized by an antibody on the array, then a magnetic signal will be detected at a position on the support that corresponds to the antibody-protein complex. Since each antibody and its position on the array are known, an identification of the protein/tumor marker and, thus, the disease state of the subject, are rapidly determined. Additionally, one embodiment can employ nucleic acid probes joined to a support to form an array of magnetically labeled nucleic acids from a biological sample from a human subject. In this manner, by way of example, disease prognosis may be assessed based on the use of nucleic acid probes which are associated with sequences that have been associated with human disease and the detection of magnetically labeled complementary nucleic acid sequences present in the biological sample. These approaches are easily automated using technology known to those of skill in the art of high throughput diagnostic analysis.

The present invention may comprise in its embodiments any addressable array technology known in the art. One embodiment of polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods, which incorporate a combination of photolithographic methods and solid phase oligonucleotide synthesis. (See Fodor et al., *Science,* 251:767-777, (1991)). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143, 854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

Preferred embodiments of the present invention include several methods and systems to detect the magnetic signal of a magnetic label that is attached to a biomolecule. Although many biological molecules incorporate iron, biological materials generally exhibit no net magnetic field. (See Stryer, L., *Biochemistry* (1993)). Accordingly, the magnetic signal generated by a magnetic label attached directly or indirectly to a biomolecule is accurately measured and characterized with a high degree of sensitivity and little background noise.

For embodiments that simply detect the presence of a magnetic label on a support (and, hence, whether the biomolecule is attached to a magnetic label), a magnetic sensor such as an inductive read head (e.g., the read head used in a Toshiba model KT-53 stereo cassette) can be used. In contrast, when a relatively precise measurement of the strength of the magnetic field generated by the magnetic label is desired to ascertain not simply the presence of the magnetic label attached to a biomolecule on a support but also the location of the biomolecule, the sensor is desirably a magnetoresistive (MR) read head, as examples only, the read heads used in certain existing disk drives and/or the MR heads made by IBM of Armonk N.Y. or Eastman Kodak Co. of Rochester N.Y. and disclosed by Smith et al. in *J. App. Physics* 69(8):5082 (1991). In some embodiments, the invention uses a MR sensor that is embedded in a chip, wherein the chip has a surface to accommodate the deposit of biomolecules. In other embodiments, the sensor may be a magnetic force microscope, SQUID sensor, metal film Hall-effect device, or a ultra-high sensitivity susceptometer (for sensing paramagnetic and superparamagnetic markers), such as the device disclosed by Slade et al. in *IEEE Transactions on Magnetics*, 23 (5):3132 (1992).

In one embodiment, a sensitive giant magnetoresistive ratio sensor on a solid-state chip ("GMR Sensor") is used in a magnetic detection system to identify the presence of a magnetic label attached to a biomolecule. The GMR sensor, which may run on very low wattage, is a rugged solid state chip which is mass produced inexpensively. The utility of the GMR based sensor is highlighted in one respect by its sensitivity to small changes in a nearby magnetic field. GMR materials exhibit an order of magnitude greater sensitivity to changes in magnetic field strength than standard anisotropic magnetoresistive materials and saturate at larger fields yielding an improved dynamic range. (See Daughton, J. et al., *IEEE Trans. Mag* 30 (1994), Barnas, J. et al. *PhysiRevi B* 42:8110(1990)).

A GMR sensor may be used in the configuration illustrated in FIG. 1. A commercially available sensor 1 (model T15, Nonvolatile Electronics Inc., Eden Prairie Minn.) is coupled to a power supply 2. The sensor 1 advantageously includes biasing magnets for producing an applied biasing magnetic field 3. The input voltage on line 4 and the output of the sensor on line 5 are routed to an operational amplifier 6, and the output signal 7 is measured. This output signal 7 will vary with variations in the intensity of an externally applied magnetic field 8.

A generous dynamic range is obtained by the GMR sensor because the final voltage output depends on the sensitivity and range of the GMR sensor chip, the applied magnetic field, and the input voltage. That is, for any given GMR chip both the offset magnetic bias and the input voltage are easily manipulated to allow for a wide range of detection sensitivity.

GMR materials may be composed of alternating 15-40 Å layers of ferromagnetic metals such as CoFe, NiFeCo and alloys such as CuAgAu. To make a sensitive magnetic sensor, the GMR materials may be etched into four resistors on a chip hooked together in a Wheatstone bridge with two of the resistors shielded from magnetic fields. When an external magnetic field is applied, the resistance of the two unshielded GMR material resistors changes and unbalances the bridge. When an input voltage is put across the bridge, the output voltage increases with the application of a magnetic field. The output voltage is desirably read directly or, for small applied fields, the voltage deviation from the offset voltage is amplified with a commercially available op-amp, as illustrated in FIG. 1. The output voltage is preferably displayed using a digital oscilloscope program running on a personal computer, for example. A desirable detection system is disclosed in the published PCT application having International Publication No. WO 96/05326 to Fox, the disclosure of which is incorporated by reference herein in its entirety.

Figure 2:
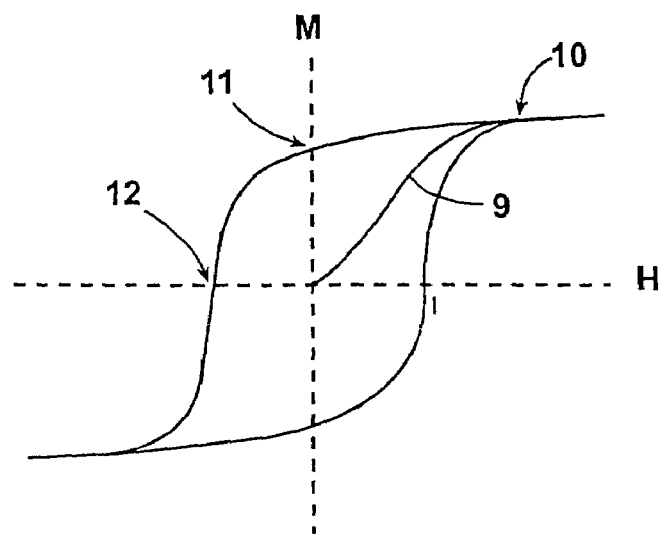
FIG. 2 is a graph of a hysteresis loop for a ferromagnetic material.

In one embodiment of the invention, the measured magnetic signal is used not only to determine the presence of magnetic label but also to distinguish between different magnetic labels. One of ordinary skill in the art will appreciate generally that different magnetic materials have different magnetic properties. In addition to the fundamental classes of magnetic behavior mentioned above, such as paramagnetism, diamagnetism, ferromagnetism, and the like, different materials within each class have distinguishable magnetic characteristics. For example, ferromagnetic materials exhibit hysteresis in the presence of a varying applied magnetic field. This is illustrated in FIG. 2, which shows a graph of magnetization (M) versus applied magnetic field intensity (H) for a hypothetical ferromagnetic material. If an unmagnetized sample of ferromagnetic material is subjected to an increasing applied magnetic field intensity, the magnetization of the material will increase along line 9 of FIG. 2. As the field strength is increased, the material reaches a saturation magnetization 10 and no further magnetization takes place as the applied field is increased. Following saturation, if the applied field is slowly reduced, the magnetization of the material will also be reduced. Upon return to zero applied field, however, a remnant magnetization 11 will remain. If the direction of the applied field is then reversed and increased slowly from zero in the opposite direction, the remnant magnetization will be reduced as the material begins to re-orient in the new direction of the applied magnetic field. The applied field strength required to eliminate the remnant magnetization so that the material is demagnetized is known as the coercive force 12. If the field is increased still further in the opposite direction, the material will become increasingly magnetized in that direction, until saturation is again reached, but in the opposite direction. Reducing the field to zero again results in a remnant magnetization of the same magnitude as the first, but of the opposite polarity. This process of magnetization under an applied field defines a "hysteresis loop" that is characteristic of the material. The three parameters of the hysteresis loop described above, saturation magnetization, remnant magnetization, and coercive force, are each different for different types of ferromagnetic material, and thus, magnetic probes or labels made from different types of material may be distinguished based on these differing magnetic properties.

The present invention also includes methods and systems to assess ratios of these parameters. For example, the ratio of remnant magnetization to the saturation magnetization is known as the "remnant squareness" of the hysteresis loop. The slope of the M-H curve when the hysterisis loop crosses zero magnetization (i.e., at the coercive force designated 12 in FIG. 2) is also a characteristic of the material. Another parameter known as "loop squareness" approaches 1 as the hysteresis curve at this point becomes increasingly vertical. These other parameters derived from the hysteresis curve may be especially useful in differentiating magnetic labels, as the measured numerical value of a ratio of measurements or a rate of change of magnetization can be less dependent on the concentration of label in the sample being measured.

Figure 3:
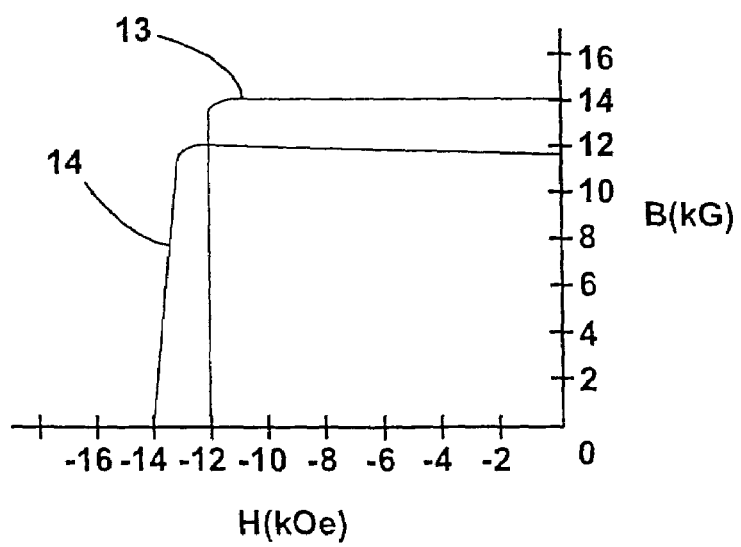
FIG. 3 is a graph of a portion of the hysteresis loops for neodymium iron boron and samarium cobalt.

In FIG. 3, a graph illustrating magnetization as a function of applied field intensity is provided for two different materials. This graph shows the upper left quadrant of the hysteresis curve for neodymium iron boron 13, and for samarium cobalt 14. It can be seen from examination of this Figure that the neodymium iron boron material has a higher saturation magnetization, lower coercive force, and steeper slope at zero magnetization. These features may be used to distinguish the presence of magnetic labels made from different materials.

Embodiments of the present invention measure the magnetization of a selected sample material as a function of applied magnetic field strength. From these measurements, aspects of the hysteresis loop exhibited by the sample are determined. Three types of equipment frequently used to characterize the magnetic properties in materials are the 60-Hz M-H looper, the toroidal B-H looper, and the vibrating sample magnetometer (VSM). Any of these commercially available instruments, or other comparable equipment or systems, can be used to measure magnetic properties of labels. Therefore, a sample containing a magnetic label of a first kind is distinguished from a sample containing a magnetic label of a second kind. Typically, and as illustrated by FIG. 3, the different labels will have different chemical composition. For example, they can comprise two different iron alloys, or an iron based label and a rare earth element based label. Samples containing these labels will exhibit hysteresis loops having different shapes, and are thus distinguishable with magnetization analysis under an applied external magnetic field. Mixtures of two different labels are also detectable because the sample will exhibit a hysteresis loop having characteristics that are intermediate between the loops exhibited by the two labels individually.

The present invention also includes methods and systems to detect and characterize magnetic labels attached to a biomolecule disposed on a support. Because magnetic labels attached to a biomolecule generate a quantifiable magnetic field, the presence and location of biomolecule on the support can be determined. For example, in one preferred embodiment, when a support having a biomolecule attached to a magnetic label is juxtaposed with a magnetic sensor and moved past the magnetic sensor, the magnetic field of the attached magnetic markers variably permeate the sensor and thereby cause the sensor to generate a detection signal. For label characterization, an external magnetic field is applied, and sample magnetization is measured at a plurality of applied field strengths. When detecting the presence of label, the support is preferably closely juxtaposed with the sensor and, more preferably, the substrate is distanced from the sensor, by way of examples only, by only a few microns or less, so as to improve the sensitivity of detection. In other embodiments, the support and the sensor may be integrated. The sensor is electrically connected to a signal processor that receives the detection signal and generates a signal representative of the amount of magnetic label present.

The signal processor includes signal processing circuitry known in the art for processing signals from magnetic sensors, as well as a correlator for generating a biomolecule concentration based upon the detection signal from the magnetic sensor. For example, the correlator can be a programmable chip or a microprocessor having software which interprets the magnetic signal information to calculate and display biomolecule concentration. Desirably, the correlator is calibrated to generate accurate biomolecule concentration by means well-known in the art, e.g., by passing several supports having known quantities of a biomolecule deposited thereon next to the sensor and adjusting the resulting detection signals to the known concentrations. Additionally, the signal from the signal processor can be sent to an output device.

If desired, the present invention may also include a transporter and a support that can be positioned on the transporter to move the support past the sensor. In one embodiment, the sensor is moved past the substrate in a raster-scan type motion to generate a two-dimensional data output, e.g., an image, having an "x" dimension and a "y" dimension. Further, the two-dimensional data output can be transformed into a three-dimensional output wherein the third dimension ("z" dimension) represents magnetic signal intensity.

Preferred embodiments of the invention provide methods and systems to attach a biomolecule with a detectable magnetic label. In some embodiments, a biomolecule is directly attached to a magnetic label (e.g., by an interaction with a ferrofluid) and in others the biomolecule is indirectly attached to a magnetic label (e.g., by an interaction with a magnetically-labeled protein, as described below). Positively charged ferrofluids offer many advantages over other types of magnetic labels. These ferrofluid magnetic labels have no special storage, handling or disposal requirements and are relatively easy to fabricate. Ferrofluids are commercially available and ferrofluids having many different types of magnetic particles and, thus, different magnetic properties, can be custom-made and obtained through Ferrofluidics, Nashua, N.H. Each particle in a ferrofluid has an intrinsic magnetic moment that can be aligned and accentuated with the application of an external orienting field. In solution, ferrofluids exist in a colloidal state but when ferrofluids bind to a biomolecule their colloidal properties diminish. Additionally, ferrofluids in a colloidal state are not strongly attracted by a magnet, however, when bound to a biomolecule, the magnetic properties of a ferrofluid permit magnetic attraction. A ferrofluid's loss of colloidal properties upon binding to a biomolecule and the ability to attract biomolecules bound to a ferrofluid with a magnet are exploited by the invention to separate ferrofluid-bound biomolecules from biomolecules and ferrofluid which have not interacted.

In some embodiments, a ferrofluid is attached to a biomolecule (e.g., a probe for the detection of a specific nucleic acid sequence or protein domain) and separated from unbound biomolecules and unbound ferrofluids in many ways. In one embodiment, a biomolecule is contacted with a ferrofluid for a time sufficient to allow the magnetic label to interact with the biomolecule. Subsequently, centrifugation is performed to loosely pellet the biomolecules having attached magnetic labels. The supernatant is removed and the pellet is resuspended in distilled water or a suitable buffer. This "washing" procedure is desirably performed several times so as to effectively remove all the unbound ferrofluid and unbound biomolecules. The unbound colloidal ferrofluid and unbound biomolecules remain in solution, while the ferrofluid bound to the biomolecule is pelleted and, thus, separated from the unbound ferrofluid and unbound biomolecules.

In another embodiment, a magnet is used to separate biomolecules bound to a ferrofluid from unbound ferrofluids and unbound biomolecules. As above, a biomolecule is contacted with a ferrofluid for a time sufficient to allow the magnetic label to interact with the biomolecule. Subsequently, a magnet is applied, for example, to the side of the vessel housing the biomolecule and ferrofluid, and the biomolecules having attached magnetic labels are aggregated near the magnet. The supernatant is carefully removed and the magnetic aggregate is resuspended in distilled water or a suitable buffer. This "washing" procedure is desirably performed several times so as to effectively remove all the unbound ferrofluid and unbound biomolecules. The unbound colloidal ferrofluid and unbound biomolecules remain in solution, while the ferrofluid bound to the biomolecule is aggregated and, thus, separated from the unbound ferrofluid and unbound biomolecules.

As indicated above, embodiments of the present invention include the use of positively charged ferrofluid colloids to directly label a probe biomolecule. Such techniques can also be used in the invention to label a biomolecule disposed on a support so as to detect its presence and location. The detection of a biomolecule disposed on a support, for example, is accomplished by applying the ferrofluid to the biomolecule, washing away unbound or non-specifically bound ferrofluid, and detecting the magnetic signal generated by the bound magnetic label. From the information generated by the magnetic signal from the support, the presence and location of the biomolecule are determined.

The invention also includes methods and systems to attach a magnetic label to a target biomolecule indirectly by binding a magnetically labeled secondary molecule to the target biomolecule. In addition to the use of magnetically labeled probe biomolecules to detect specific sequences or proteins, as will be discussed below, magnetically labeled secondary molecules, as examples only, nucleic acids or proteins, are used to detect biomolecules disposed on a support. As examples, and without limitation, in some embodiments a magnetic label is attached to a nucleic acid which interacts with a protein binding domain such as found in transcription factors or other nucleic acid binding proteins. In other embodiments, a magnetic label is attached to a protein which interacts with a modified nucleotide within a nucleic acid sequence or a modified domain of a protein. In the latter instance, magnetically labeled antibodies specific for modified biomolecules, such as dinitrophenol (DNTP), isopentenyl-6-adenosine ($I_6A$), and biotin, are used. Additionally, biotin residues on a nucleic acid or protein are readily detectable with embodiments that use magnetically labeled avidin, streptavidin, monomeric avidin, and derivatives or modifications of these proteins. Accordingly, these proteins are preferably labeled with a ferrofluid and are separated from unbound protein and ferrofluid by the methods detailed above, however, several commercially available magnetic antibodies and magnetic avidin and streptavidin are available.

Embodiments of the invention also include methods and systems to detect specific biomolecules within a population of heterogeneous biomolecules disposed on a support. One of ordinary skill in the art will appreciate that many conventional approaches to specific nucleic acid detection, such as Northern and Southern hybridization, and specific protein detection, such as Western blotting and immunoprecipitation, are adaptable for use with embodiments of the present invention. In some embodiments of the present invention, a non-magnetic colloid or other blocking agent which binds to single stranded nucleic acid or non-specific binding sites on a target biomolecule are added. Non-magnetic colloids, such as silver stain, and blocking agents, such as Salmon sperm DNA, carrier RNA, bovine serum albumin, ovalbumin, and casein, are added to reduce non-specific binding of probes and background noise.

One embodiment of the invention identifies a specific biomolecule (e.g., proteins or nucleic acids) within a population of heterogeneous biomolecules is as follows: First, a sample having a target biomolecule, among a heterogeneous population of biomolecules, is disposed on a support. The target biomolecule on the support is then contacted with a magnetically-labeled probe biomolecule that interacts with the target biomolecule. The unbound and nonspecifically bound magnetic probe is removed by washing in a suitable buffer, and the bound magnetic signal is measured and characterized with a magnetic sensor, as described above. Accordingly, the presence of a magnetic signal at a specific location on the support identifies the presence of the target biomolecule. Alternatively, as discussed above, one or several different probe biomolecules can be disposed on a support at different locations so as to create an addressable array that is used to detect the presence of one or more target biomolecules in a preparation of biological sample. Magnetically labeled biomolecules present in the biological sample are applied to the array, the support is washed so as to remove unbound and nonspecifically bound biomolecules, and the magnetic signal that remains on the support is detected using a magnetic sensor, and the presence of the target biomolecule in the biological sample is identified.

In other embodiments, many different probes or biological samples or both are screened at the same time. By using a method referred to as "multiplexing", the invention screens biomolecules present in several biological samples, including samples from different individuals, against a battery of probe biomolecules in the same reaction to determine predispositions to disease, genetic typing, and forensic identification, as examples.

In one embodiment, an addressable array is constructed wherein many different probe biomolecules (e.g., nucleic acid probes or antibodies or other types of protein probes) are disposed on a support at locations that are separate from one another and readily identifiable. The locations and identities of the probe biomolecules on the support are recorded (e.g., on a recordable computer media such a computer disk, hard drive, CD ROM, DVD ROM, or other recordable media as known in the art). Biological samples from three individuals, for example, having biomolecules that correspond or are detectable by probes on the array if the target biomolecule is present are obtained and prepared, according to conventional techniques in hybridization or blotting or both. The three different biological samples are separately labeled with different magnetic labels (e.g., ferrofluids) such that the first is labeled. The magnetically labeled biological samples are washed so that only specifically bound magnetically labeled biomolecules remain in the samples and the samples are pooled.

The pooled sample now comprises the biomolecules of three different individuals and three different magnetic labels. The pooled sample is then contacted to the array under conditions which allows for specific binding of the probe biomolecules to any target biomolecules that may be present in the three different samples. The unbound and nonspecifically bound biomolecules are removed by washing in a suitable buffer, and the array is passed before a magnetic sensor which characterizes and measures the magnetic signals bound to the support in an applied magnetic field, for example. Because each of the three different magnetic labels has a magnetic particle that has a unique magnetic signal (e.g., hysteresis curve shape and slope, saturation magnetization, remnant magnetization, coercive force, etc.), the identity of the presence or absence of each type of magnetic particle can be accomplished in the same reaction. Thus, the detection of one, two, or three magnetic signals from one or more locations on the array can be accomplished using this embodiment of the present invention, and the ability to rapidly screen several individuals for many different indicators for disease and genetic composition has been accomplished.

As one of ordinary skill in the art will readily recognize embodiments of the multiplexing method of the invention can be used to screen a single individual against a battery of magnetically labeled probes. Accordingly, different types of probe biomolecules (e.g., protein or nucleic acid) are labeled with unique magnetic particles so that the presence of multiple probe biomolecules bound to target biomolecules (e.g., protein or nucleic acid) from a biological sample from the individual can be accomplished. A biological sample from the individual to be screened is obtained and prepared and the biomolecules to be probed are disposed on a support. The various magnetically labeled probes are contacted with the biomolecules on the support, the unbound and nonspecifically bound probes are removed by washing, and the magnetic signals are detected and resolved, as described above.

Additionally, multiplexing embodiments of the invention may perform dynamic competitive binding studies. In one embodiment, a target biomolecule (e.g., protein or nucleic acid) is disposed on a support or several target biomolecules (e.g., proteins or nucleic acids) are disposed on a support so as to create an addressable array. Two or more probe biomolecules (e.g., protein or nucleic acid) that are thought to compete with one another for the same target biomolecule are joined with different magnetic labels, as described above. Thus, the competing probe biomolecules have magnetic labels that provide magnetic signals which can be resolved from one another. The competing probe biomolecules are contacted with the target biomolecule(s) under conditions that allow for binding and the unbound or nonspecifically bound probes are removed by washing. The support is then passed before a magnetic sensor, the magnetic signals are detected and resolved, and competitive inhibition is determined. In additional embodiments, the support and sensor may be integrated. Desirably, the binding kinetics of the competition are performed over time at varying concentrations of the different probes. By using multiplexing, the competitive inhibition of many different probe biomolecules can be determined in the same reaction.

The invention includes embodiments which identify an interaction of a probe with a target biomolecule in a heterogeneous sample solution. In additional embodiments, the invention detects the presence of target biomolecules in solutions, such as biological fluids obtained from a test subject. An embodiment to rapidly detect one or more target biomolecules in a solution uses colored beads onto which one or more probe biomolecules are joined, referred to as a "colored bead-probe reagent". For example, a colored bead-probe reagent is generated by an approach described above, and magnetically labeled biomolecules that are obtained and prepared from a biological sample from a subject are contacted with the colored beads that are joined to the probe biomolecules. If a target biomolecule is present in the biological sample, then a colored bead-probe-target biomolecule complex will form. Since the target biomolecule is labeled with a magnetic probe, the colored bead-probe-target biomolecule complex can be separated from the unbound colored beads joined to probe biomolecules with a magnet. In a preferred embodiment, a bar magnet is applied to the side of the reaction vessel to aggregate the colored bead-probe-target biomolecule complexes and quickly identify the presence of the target biomolecule in the biological sample. By using several different colored beads, each color having a probe biomolecule that detects the presence of a different target biomolecule, multiple target biomolecules can be detected in the same reaction. A colored mixture of beads obtained in a given reaction can be compared to a color chart to rapidly identify the presence and amount of target biomolecule in a biological sample.

Additionally, in some embodiments, an optical device, such as spectrophotometer or a photodiode CCD camera, is employed to more accurately measure the binding of a probe biomolecule to a target biomolecule and to determine the relative amount of target biomolecules in the reaction. For example, after the aggregated colored bead-probe-target biomolecule complexes are separated from colored bead-probe reagents that failed to bind to a target biomolecule, the colored bead-probe-target biomolecule complexes are resuspended in a solution and the absorbance of light is determined by conventional spectroscopy. By using colored bead standards (e.g., a known quantity or mixture of colored beads having reproducible absorbance values), one of ordinary skill in the art can accurately determine the amount of colored bead-probe-target biomolecule complex present in the solution and, thereby, determine the amount of target biomolecule present in the biological sample. Similarly, varying shades of colored beads are detectable when more than one color of bead-probe reagent is used to detect multiple target biomolecules and the presence of the various target biomolecules is determined by comparing absorbance readings at different wavelengths and comparing these values to standards.

Additional embodiments may include, as examples only, fluorescent beads or fluorescent cells which produce fluorescent signal (for example, like green fluorescent protein), with subsequent measurement of fluorescence.

Additional embodiments of the present invention include competitive inhibition assays using multiple colored beads Accordingly, a magnetically labeled target biomolecule is placed in a solution comprising two or more competing probes (e.g., probes that compete for the same binding site) that are joined to different colored beads. Binding is allowed to occur and a magnetic field is applied to the reaction so as to allow for the aggregation and separation of colored bead-probe-target complexes from the colored bead-probe reagent that failed to form a complex with the target biomolecule. The relative binding of each probe is resolved by visually determining the amount of binding of each colored bead, according to a visual inspection of a color chart, or more precise measurements may be obtained by employing an optical device, such as a spectrophotometer or CCD camera, as described above.

Another embodiment of the present invention detects target biomolecules in a solution by monitoring magnetic swing time. "Magnetic swing time" means the time it takes for a magnetic compound to reorient itself to a changed magnetic field. For example, when a single magnetic particle is attached to a biomolecule, this magnetic-biomolecule complex will orient itself in a solution according to the magnetic field placed near the complex. If the magnetic field direction is then moved by 90°, a period of time is required for the magnetic biomolecule complex to reorient itself to the new field position. The measurement of the time it takes for the magnetically-labeled molecule to reorient itself to the changed magnetic field is referred to as magnetic swing time.

The present invention measures magnetic swing time to determine when a magnetically labeled biomolecule has complexed with another biomolecule. That is, the binding of a target biomolecule by a magnetically labeled probe molecule provides a greater mass and, thus, a greater swing time than the unbound magnetically labeled probe. By measuring the time that is required for the magnetic particles to reorient themselves to the changed magnetic field, the mass of the magnetically labeled complex can be determined. For example, if the mass has increased (by binding the target biomolecule), magnetic swing time will also increase when all of the other factors are held constant.

In one embodiment, a target biomolecule (e.g., a protein or nucleic acid) is suspended in a suitable buffer. In a separate vessel, a magnetically labeled probe molecule which interacts with the target biomolecule is suspended in a suitable buffer. A strong magnetic field is applied to the magnetically labeled probe molecule so as to orient the magnetic label to the magnetic field. Once the initial magnetic field orientation is established, the position of the magnetic field is shifted (e.g., by 90°) and the time that is required for the magnetically labeled probe to reorient itself to the magnetic field is measured. Because the strength of the magnetic field is constant and the mass of the magnetically labeled biomolecule probe is known, the acceleration of the magnetically labeled biomolecule, as a function of time, is determined.

Next, the magnetically labeled biomolecule is brought in contact with the target biomolecule so as to permit the formation of a target biomolecule-probe complex. After sufficient time for binding is allowed and all unbound probe is removed from the vessel by washing, a strong magnetic field is applied so as to orient the target biomolecule-probe complex. Once orientation to the magnetic field is achieved, the magnetic field is shifted (e.g., by 90°) and the time to reorient to the new field location is measured and recorded. A difference between the magnetic swing of the probe biomolecule in an applied magnetic field and the target biomolecule-probe complex in an applied magnetic field indicates that a binding of the target biomolecule and the probe biomolecule has occurred.

Although embodiments described above use a magnetically labeled biomolecule probe, other embodiments may use a bead that polarizes light. In this embodiment, calcite beads can be used, but fluorescent beads or fluorescent cells which emit polarized light could be employed. Next, the magnetically labeled biomolecule is brought in contact with the target polarized beads biomolecule so as to permit the formation of a target biomolecule-probe complex. After sufficient time for binding is allowed and all unbound probe is removed from the vessel by washing, a strong magnetic field is applied so as to orient the target biomolecule-probe complex. Polarized light orientation and intensity are measured. The magnetic field is shifted (e.g., by 90°) and change in the polarized light orientation and intensity are measured and recorded. A difference between the orientation and intensity of the light indicates that a binding of the target biomolecule and the probe biomolecule has occurred. The embodiments described above provide another very sensitive method for determining that a binding interaction between two biomolecules has occurred.

The invention includes methods and systems to enhance the binding of a probe biomolecule to a target biomolecule and to reduce non-specific binding and background noise. In one embodiment, a target biomolecule (e.g., a nucleic acid or protein) is disposed on a support and is contacted with a probe biomolecule having an attached magnetic label, as described above. To enhance binding, a magnetic field is applied to regions of the support near the target biomolecule so as to induce the magnetically labeled probe biomolecule to move toward and concentrate at the position corresponding to the target biomolecule. In this manner, a greater binding to the probe biomolecule is obtained. Additionally, an electric field is applied in conjunction with the magnetic field so as to enhance the movement toward and concentration at the site near the disposed target biomolecule. In another embodiment, an electrical field or a magnetic field or both are applied to the support after binding of the target biomolecule by the magnetically-labeled probe so as remove or separate from the target biomolecule any unbound or non-specifically bound probe biomolecule.

In some embodiments, a pulsing electrical or magnetic field is used to move the probe biomolecule toward the target biomolecule and concentrate it at that site or, alternatively, to induce the unbound probe biomolecule or non-specifically bound probe biomolecule to move away from the target biomolecule. By applying the approaches described above, a magnetically labeled probe can be concentrated at a site near the target biomolecule and thereby increase the kinetics of binding, and unbound and non-specifically bound probe can be separated from the specifically bound probe so as to reduce background.

Preferred embodiments of the invention may separate magnetically labeled biomolecules on the basis of mass by applying a magnetic field. In one embodiment, the invention provides methods and systems that separate magnetically labeled biomolecules according to their mass in an applied magnetic field. Biomolecules are first labeled with a magnetic marker, preferably a ferrofluid, for example by the approaches detailed above. Once the biomolecules are magnetically labeled, they are suspended in a solution (e.g., a suitable buffer) and a magnetic field is applied to the sample. Because the amount of ferrofluid which binds to the biomolecule is directly proportional to the mass of the biomolecule, molecules with greater mass have a greater magnetic potential than smaller molecules. Accordingly, magnetically labeled biomolecules are separated according to their mass by applying a strong magnetic field.

The following examples are provided for exemplary purposes and are not intended to limit embodiments of the present invention.

EXAMPLE 1

In this example, the present invention detects the presence and location of a nucleic acid disposed on a support by means of a magnetic label attached to a nucleic acid. As an example, one microliter containing 100 ng plasmid DNA (pHIS, ≈3700 base pairs/molecule) are spotted on a positively charged nylon membrane (Hybond, Amersham) that is subsequently cut into 1 cm×4 cm strips. The strips are air dried for 10 minutes and each strip is dipped in distilled water for 10 seconds. Next, the strips are contacted with a ferrofluid (EMG607; Ferrofluidics, Nashua N.H.) for two minutes, then washed for 2 minutes in distilled water and air dried.

Figure 4:
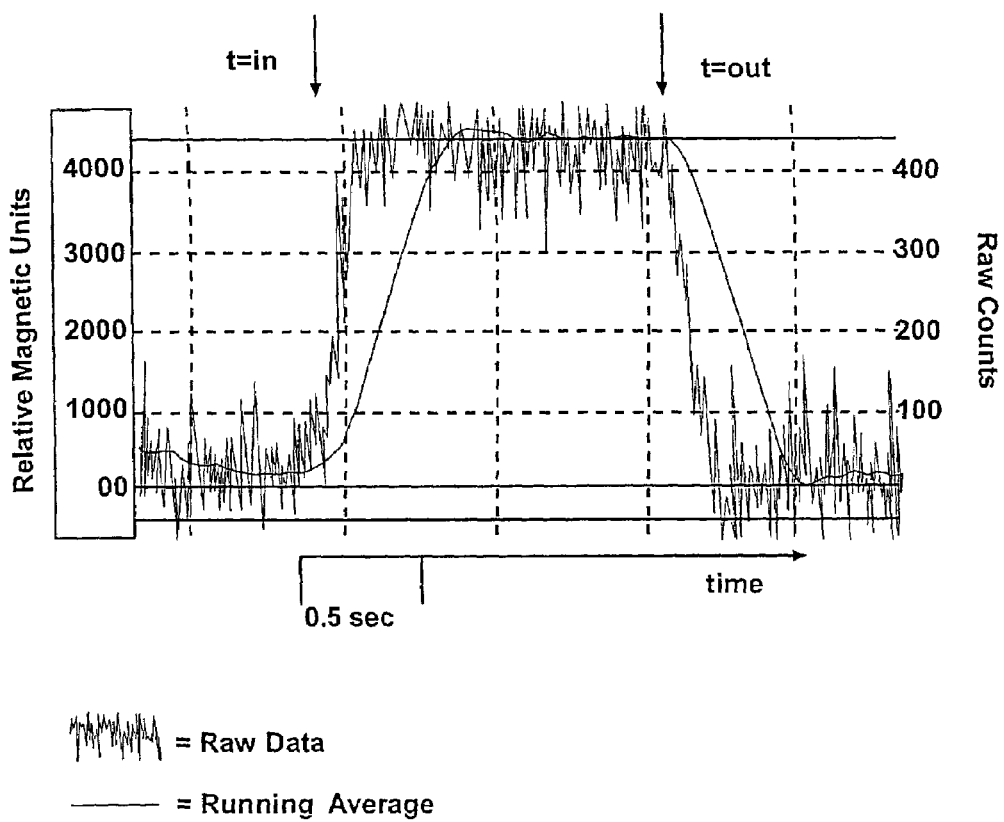
FIG. 4 illustrates a typical output of an embodiment of a magnetic detection system in which a ferrofluid-labeled DNA sample was inserted into the reader at t=in and removed at t=out; the smooth line represents a 200 point running average.

Samples are measured using a GMR sensor (T15 model; Nonvolatile Electronics Inc., Eden Prairie Minn.) with biasmagnets, and the voltages are recorded by a PC after analog processing and 12 bit A/D conversion. Output from the prototype magnetic detection system unit for the detection of nucleic acids is shown in FIG. 4. The magnetism of the DNA/ferrofluid filters is also measured with a vibrating sample magnetometer (VSM, Digital Measurement Systems Inc.) to verify and calibrate the results. The VSM determines the actual emu generated at the surface of the sample, whereas the GMR sensor determines the relative emu. Triplicate samples, prepared identically to the one used to generate the GMR sensor data shown in FIG. 4, yield an average of $4.5 \times 10^3$ ($\pm 0.7$) emu. From this data it may be determined that one relative magnetic unit (RMU) equals $\approx 10^5$ emu.

Figure 5:
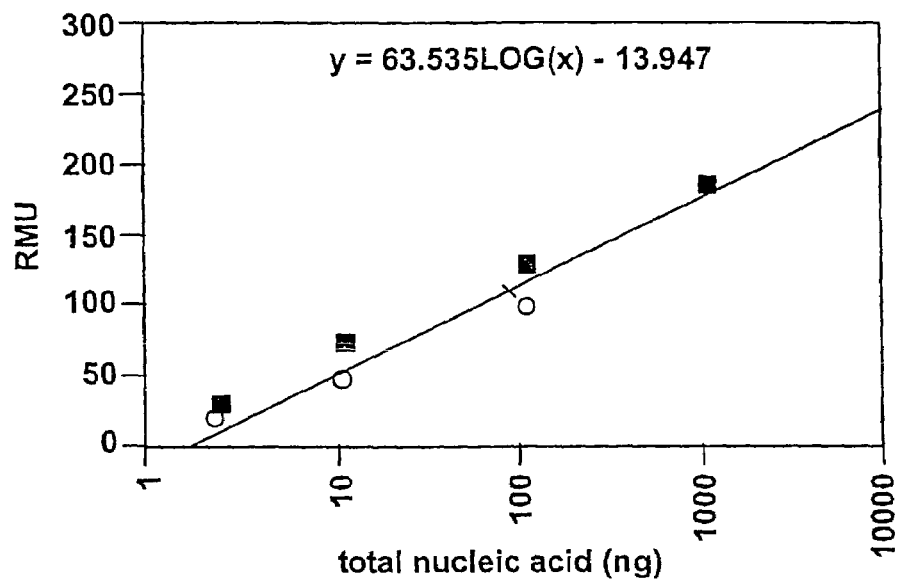
FIG. 5 shows a semi-log plot of varying amounts of ferrofluid-labeled plasmid dsDNA (■) or an oligonucleotide (○) spotted on a support and detected with an embodiment of a magnetic detection system; the relative magnetic unit reading (RMU) was the maximum voltage deflection of the spot corrected for background voltage and the line represents the mathematical fit to the data (equation is in the inset).
Figure 6:
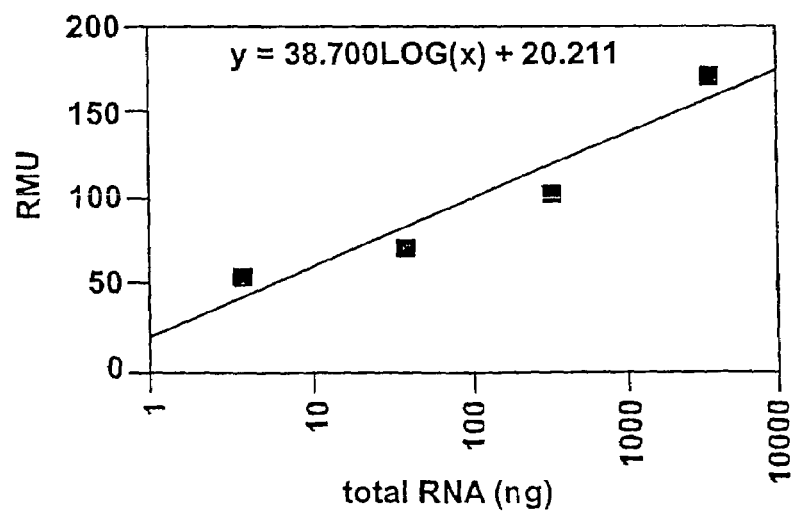
FIG. 6 shows a semi-log plot of varying amounts of ferrofluid-labeled RNA (■) spotted on a support and detected with an embodiment of a magnetic detection system; the relative magnetic unit reading (RMU) was the maximum voltage deflection of the spot corrected for background voltage and the line represents the mathematical fit to the data (equation is in the inset).

As another example, similar concentrations of double stranded plasmid DNA (dsDNA) or single stranded DNA are spotted on a membrane and the GMR sensor reader displays an linearity of response on a semi-log pilot, as shown in FIG. 5. A sensitivity of detection on the order of 2 ng/ul for both ssDNA and dsDNA is obtained. In a third example, the detection of total RNA at a similar sensitivity is demonstrated, as shown in FIG. 6. The data presented above show that a GMR sensor can detect over three orders of magnitude (microgram-to-nanogram) of dsDNA, ssDNA, and total RNA in a very small volume of sample.

EXAMPLE 2

In this example, the invention detects a protein disposed on a support. In this example, the invention detects the presence and location of a protein disposed on a support by means of a magnetic label attached to a protein. In one example, 1 ul of a solution containing either mouse IgG or goat IgG is spotted on a membrane that is subsequently cut into 1 cm×4 cm strips. The strips are then air dried and each strip is dipped in distilled water. Next, the strips are contacted with 2 ul of ferrofluid (EMG607; Ferrofluidics, Nashua N.H.). The samples are then washed, allowed to air dry, and are measured using a GMR sensor (T15 model; Nonvolatile Electronics Inc., Eden Prairie Minn.) with bias-magnets, and the voltages were recorded by a PC after processing as in Example 1. The results show that ferrofluid efficiently labeled mouse IgG and goat IgG which was disposed on a support and the proteins are effectively detected using the GMR sensor.

EXAMPLE 3

The invention also comprises hybridization using magnetically labeled nucleic acid probes are provided. In this example, the invention uses a magnetic label attached to a nucleic acid probe to detect a target nucleic acid disposed on a support. A first oligonucleotide of 52 nucleotides (T54) is used as a target nucleic acid and a second complementary oligonucleotide (T55), bound with a ferrofluid, was used as a probe nucleic acid. One microliter of the target nucleic acid T54 (at 0.5 ug/ul) is spotted on a nylon membrane and is crosslinked with UV light (autolink setting; Stratalinker 2500; Stratagene). Subsequently, the membrane is washed briefly with water and air dried. The probe nucleic acid is made by incubating 2 ug of a complementary oligonucleotide, T55, with ferrofluid (1:1 (v:v) in 10:1 total volume). Unbound T55 is separated and removed from the ferrofluid conjugated T55 by washing with water, as described above.

The hybridization is conducted as follows. The ferrofluid-labeled probe nucleic acid is suspended in 3 ml of a 1×SSC solution (Sambrook, J. et al., *Molecuclar Cloning, A Laboratory Manual* (1989)) and is placed in a 15 ml conical tube containing the support having the target nucleic acid. The hybridization is conducted in an oven at 50° C. for 16 hours. A negative control is run in parallel using T55 as both the probe and target nucleic acid. The filters are removed, washed in 1×SSC, and air dried. The relative magnetic units are then determined using the GMR sensor, as described in Example 1. The sample having the T54 target nucleic acid and the T55 probe nucleic acid yield an average of 710 (±64) RMU, whereas, the sample having the T55 target nucleic acid and the T55 probe nucleic acid had an average of 360 (±80) RMU. Moreover, when the salt concentration in the hybridization buffer is lowered, a decrease in signal for the sample having the T54 target nucleic acid bound with T55 probe was observed, indicating strand displacement. In contrast, a decrease in signal is not observed for the control when the salt concentration was lowered. These results demonstrate the invention's ability to perform nucleic acid hybridization using a ferrofluid-bound nucleic acid probe.

EXAMPLE 4

The invention also detects a target nucleic acid by using a biotinylated nucleic acid probe and a ferrofluid-labeled streptavidin marker. In this example, the invention uses streptavidin conjugated with a magnetic label to identify the presence and location of a biotinylated nucleic acid probe hybridized to a target nucleic acid disposed on a support. The probes for these experiments comprise a DNA-biotin-streptavidin-magnetic bead complex. Biotinylated 40-mer oligonucleotides complementary to a regions of the 8 phage genome are used. There are many custom service companies for oligonucleotide synthesis but, desirably, the nucleic acid probes are made on the premise using a Milligen Cyclone Plus synthesizer at the 0.012 micromole scale. Commercially available modification chemicals are used to quantitatively biotinylate the oligonucleotide directly on the synthesis column (Cruachem). There are also several commercial sources of streptavidin magnetic beads (MPG, Dynal, Promega or Boehringer Mannheim). In order to reproduce an optimum coupling efficiency, various dilutions of the 5 um beads will be contacted with the biotinylated oligonucleotide. Desirably, the highest magnetic concentration is sought so as to minimize the possibility that any given bead will have more than one oligo attached. Custom preparations of magnetic beads, having a single streptavidin molecule per bead, are also obtainable. (Bangs Labs, Fishers, Ind.).

DNA from 8 phage is isolated and a region encoding the D gene is used as the target nucleic acid. (See Mikawa et al., *J. Mol. Biol*, 262:21 (1996) for a description of suitable target nucleic acid sequences and complementary probe nucleic acid sequences). There are a number of well-known chemicals used to isolate viral RNA or DNA. (Sambrook, J. et al., *Molecular Cloning, A Laboratory Manual* 1989)). Phenol, for example, denatures the coat proteins of virus and liberates the nucleic acids inside. The proteins aggregate at the phenol/water interface and the nucleic acid remains in the aqueous phase. Phenol is, however, a moderately caustic chemical and several methods that rely on less harsh agents have been developed. Numerous formulations based on combinations of detergents (SDS, SLS, Nonidet P40, reductants (DTT and beta-ME), proteases (Proteinase K, pronase) and chaotropics (guanidine, guanidinium thiocyanate) have also been published. (Sambrook, J. et al., *Molecular Cloning, A Laboratory Manual* (1989), Luria, S. E. et al., *General Virology* and Calendar, R., *The Bacteriophages* (1988)).

Once the phage DNA is isolated, it is spotted at various concentrations on a nylon membrane and crosslinked with a standardized dose of UV light (1200 units in a Stratalinker). The filter is also, preferably, prehybridized with a non-magnetic colloid and/or a blocking agent. The filter is then brought to 6×SSC and the magnetically-labeled probe (biotinylated oligonucleotide bound to magnetically-labeled streptavidin) is added. Hybridization is conducted for 16 hours at 20° C. below the calculated $T_m$. After washing, the sample is measured for magnetic activity with a GMR sensor, as described above. As a negative control, 8 DNA is spotted on the filter and hybridized with a non-complementary oligonucleotide coupled to a magnetic bead. As a positive control, a biotinylated oligonucleotide probe is labeled with a streptavidin-alkaline phosphatase conjugate and the filter is developed with standard precipitating substrates. These results demonstrate that nucleic acid hybridization using magnetically-labeled streptavidin molecules bound to biotinylated nucleic acid probes can be accomplished.

EXAMPLE 5

The invention also uses nucleic acid hybridization that exploits the magnetic signal generated by a ferrofluid. In this example, the invention uses the increase in magnetic signal obtained by a nucleic acid hybrid over a single stranded nucleic acid to identify the presence and location of the nucleic acid hybrid. In this example, a first oligonucleotide of 52 nucleotides (T54) is used as a target nucleic acid and a second complementary oligonucleotide (T55), is used as a probe nucleic acid. One microliter of the target nucleic acid T54 (at 0.5 ug/ml) is spotted on a nylon membrane and is crosslinked to the membrane with UV light (autolink setting; Stratalinker 2500; Stratagene). Subsequently, the membrane is washed briefly with distilled water and is allowed to air dry. The unlabeled probe nucleic acid (T55) is suspended in 3 ml of a 1×SSC solution (Sambrook, J. et al., *Molecular Cloning, a Laboratory Manual*, (1989)).

The support having the target nucleic acid (T54) and the 3 ml of 1×SSC solution containing the unlabeled probe nucleic acid (T55) are combined in a 15 ml conical tube. The hybridization is conducted in an oven at 50° C. for 16 hrs. The negative control for the experiment is run in parallel, and uses T55 as both the probe and target nucleic acid. The experimental and control filters are removed from the oven, washed in 1×SSC, and air dried. Next, the supports are placed in a 15 ml conical tube containing a 3 ml suspension of ferrofluid (1:1 v/v). Binding of the ferrofluid to the nucleic acids present on the supports is conducted for 5 minutes. The supports are then removed and washed in 1×SSC and air dried. The magnetic signal present on the supports is then determined using a GMR sensor, as described above.

The sample having the T54 target nucleic acid and the T55 probe will have a greater average RMU than the sample having the T55 target nucleic acid and the T55 probe. Furthermore, another washing of the membrane with a lower salt concentration (e.g., 0.1 SSC) will promote strand displacement and a decrease in signal for the support having the T54 target nucleic acid will be observed. These results demonstrate that a conventional nucleic acid hybridization with an unlabeled probe can be performed and sensitive detection of nucleic acid hybrids, by using a ferrofluid after hybridization, can be accomplished.

EXAMPLE 6

The present invention also detects a target nucleic acid by using a nucleic acid probe attached to a colored bead and a ferrofluid-labeled target nucleic acid. In this example, the invention rapidly identifies the presence of a specific nucleic acid sequence in a solution. A biotinylated oligonucleotide probe complementary to a region of the 8 phage genome is used. A biotinylated 40-mer probe which complements a region of 8 can be made as described in Example 4. A colored bead onto which streptavidin is attached is used to sequester the biotinylated oligonucleotide. Streptavidin beads are common in the art and the ability to generate a colored variety is straightforward. Many activatable linkers, some of which were described above, are available and can be used to attach streptavidin to a colored bead. Further, custom preparations of streptavidin magnetic beads can be obtained through several suppliers including Bangs Labs, Fishers, Ind.

The streptavidin beads are coupled to biotinylated oligonucleotides in TBS (Sigma T6664) and are, desirably, blocked with a non-magnetic colloid or a blocking agent or both, as described previously, overnight on a shaker. The beads are collected, washed in TBS, and the unbound biotinylated oligonucleotide is removed. The amount of biotinylated oligonucleotide which binds to the streptavidin beads can be determined by using radiolabeled oligonucleotides of a known specific activity.

Once the colored beads have been coupled to the biotinylated oligonucleotide, this immobilized probe is suspended in 3 ml of a hybridization solution having DNA isolated from the 8 phage that has been magnetically labeled. Many hybridization solutions are known (see e.g., Sambrook, J. et al., *Molecular Cloning, A Laboratory Manual* (1989)) and a 1×SSC solution with a blocking agent such as Salmon Sperm DNA or carrier RNA is desirable. Prior to hybridization, the isolated DNA is attached to a magnetic label (e.g., a ferrofluid) by using the approaches detailed above. Hybridization to the immobilized probe which complements a region of the D gene of the 8 phage, is conducted at 37° C. for 16 hrs in a 15 ml conical tube. Subsequently, the colored beads are brought to the bottom of the conical tube, washed several times in 1×SSC, and are resuspended in a 1×SSC solution. Next, a thin bar magnet is applied to the side of the conical tube and the colored beads having the biotinylated probe hybridized to a ferrofluid-labeled target nucleic acid aggregate near the magnet. In this manner, the rapid identification of the presence of a target nucleic acid in a solution is determined.

EXAMPLE 7

The invention also detects several target nucleic acid sequences in a sample by using multiple magnetically labeled probes. In this example, the invention identifies multiple target nucleic acid sequences in a biological sample having polynucleotides in the same reaction by using multiple magnetically labeled nucleic acid probes. The nucleic acid present in 8 phage are isolated by conventional techniques and are disposed on a support (e.g., membrane or chip). The nucleic acid on the support is then contacted with at least two nucleic acid probes which complement a different nucleic acid sequence present in the phage genome. For example, a first nucleic acid probe complements one region of the gene encoding the D protein and the second nucleic acid probe complements a second region of the gene encoding the D protein.

The first nucleic acid probe also has a magnetic label that is different, (therefore having a different magnetic characteristic), from the second nucleic acid probe. For example, the magnetic particles for the two probes is made of different iron or transition metal alloys having different hysteresis characteristics. It will be appreciated that more than two nucleic acid probes can be used, in accordance with this embodiment, to detect multiple target nucleic acid sequences present in a biological sample, so long as each nucleic acid probe has a different magnetic label.

The magnetic labels (e.g., ferrofluids) are attached to the probe nucleic acids according to the approaches detailed above. The support having the 8 DNA is preferably prehybridized in a solution having a non-magnetic colloid and/or a blocking agent for 2 hours at 37° C. The magnetically labeled probes are added to the prehybridized support in a hybridization solution and hybridization is allowed to occur for 16 hours at 37° C. Prehybridization and hybridization solutions are described in Sambrook, J. et al., *Molecular Cloning, a Laboratory Manual* (1989) and the conditions for hybridization may vary depending on the nucleic acid probes used and the nucleotide composition of the target nucleic acid sequences.

After hybridization, the unbound and non-specifically bound probes are removed by washing in a suitable wash buffer (e.g., 2×SSC) and the presence of a hybrid containing the first magnetically-labeled nucleic acid probe and a second hybrid having the second magnetically-labeled nucleic acid probe is detected. If the biological sample contains a nucleic acid sequence which complements the first and/or the second nucleic acid probe, then a magnetic signal which corresponds to the first and/or the second magnetic label will be detected by analyzing, for example, the magnetic hysteresis characteristics of the biological sample. Thus, rapid diagnostic screening using multiple nucleic acid probes having different magnetic labels can be accomplished.

EXAMPLE 8

The invention also detects a target protein disposed on a support by using a magnetically labeled probe. In this example, the invention specifically identifies proteins disposed on a support by a magnetically labeled probe. In the example, the probe is composed of a mouse anti-Epidermal Growth Factor (EGF) antibody (Sigma E2635) which is attached to a magnetic label (e.g., a ferrofluid). To prepare the probe, the anti-EGF antibody is coupled to a ferrofluid, as described above. The target protein is mouse Epidermal Growth Factor (EGF) isolated from submaxillary glands of mice. (Sigma E6135). Epidermal growth factor (EGF) is a 6 kD polypeptide originally discovered and purified from mouse submaxillary glands. (Levi-Montalcini and Cohen, *Ann. N. Y. Acad. Sci.*, 85:324 (1960) and Cohen, *J. Biol. Chem.*, 237:1555 (1962)).

Varied concentrations of the target protein are spotted onto a nylon membrane and the protein is immobilized to the membrane by heating under vacuum. The supports having the bound target protein are placed in a 15 ml conical tube and the support is blocked in a solution of 5% w/v BSA in TBS (Sigma) for 2 hrs. at room temperature. Other blocking agents or a non-magnetic colloids or both may be added. The blocked support is then overlayed with 3 ml of ferrofluid-labeled anti-EGF antibody suspended in the blocking buffer at an appropriate dilution (generally 1:50-1:500). Binding is then allowed to occur for 1-3 hrs. at room temperature on a shaker. The support is subsequently washed in TBS and the target protein-probe complex is detected by passing the membrane before a GMR sensor, as described above. Once the magnetic signal is determined, the probe can be stripped using conventional techniques, and the blot is reprobed with a control antibody (e.g., ferrofluid-labeled anti-bovine IgG) (Sigma B6901), according to the technique outlined above. Alternatively, a side-by-side immunoblot with the control antibody can be performed. After binding of the control antibody is allowed to take place, the support is washed, and the presence of bound antibody is ascertained by passing the support before a GMR sensor. The results of this example demonstrate that protein identification using a ferrofluid-labeled antibody can be accomplished.

EXAMPLE 9

The invention also comprises methods and systems that use immunoblotting techniques. In this example, the invention provide method and systems that use ferrofluids bound to an antibody-target protein complex to identify the presence of a specific protein in a population of heterogeneous proteins. The probes in this example are the ferrofluid-labeled anti-EGF antibody (experimental) and the ferrofluid-labeled anti-bovine IgG antibody (control), as described above. Total protein is isolated from mouse submaxillary glands by conventional techniques. Levi-Montalcini and Cohen, *Ann. N. Y. Acad. Sci.*, 85:324 (1960) and Cohen, *J. Biol. Chem.*, 237:1555 (1962). The isolated total protein (5-20 ug per well) is then separated on a 15% SDS/PAGE. Subsequently, the proteins are transferred to a nylon membrane by electroblotting and the membrane is heated under vacuum to immobilize the proteins. Next, the membrane is blocked in a solution of 5% w/v BSA in TBS for 2 hrs. at room temperature. Other blocking agents or a non-magnetic colloids or both may be added.

The ferrofluid-labeled antibody probes are then applied to the protein-bound support in 5 ml of TBS having an appropriate dilution of the antibody (generally 1:50-1:500). The blotting is allowed to occur for 1-3 hrs. at room temperature on a shaker. The support is then washed in TBS, air dried, and passed before a GMR sensor to detect the magnetic signal present on the support. As a positive control, purified EGF (Sigma) is separated on the SDS/PAGE gel. After the magnetic signal present on the support have been determined, the probes are stripped according to conventional techniques, and the blot is reprobed with the anti-bovine IgG ferrofluid-labeled antibody (control). Alternatively, total submaxillary gland proteins is separated on a duplicate SDS/PAGE gel, transferred to a membrane, and probed with the ferrofluid-labeled control antibody. These results demonstrate that the detection of a specific protein in a population of heterogeneous proteins using a ferrofluid-labeled antibody specific for the target protein can be accomplished.

EXAMPLE 10

In this example, the invention provide methods and systems to identify an antibody-target protein complex by labeling the complex with a ferrofluid and detecting its presence and location using a GMR sensor. Similar to the example above, the probes in this example are the anti-EGF antibody (experimental) and the anti-bovine IgG antibody (control). The target protein is EGF. As in Example 9, total protein from the submaxillary glands from mice (5-20:g per well) is isolated and separated on a 15% SDS/PAGE. As a positive control, purified EGF (Sigma) is also separated on the gel. The separated proteins in the gel are transferred by electroblotting to a membrane and are immobilized to the support by heating under vacuum. The support is then blocked for 2 hrs. at room temperature on a shaker in a solution of 5% BSA w/v TBS (Sigma). Other blocking agents or a non-magnetic colloids or both may be added.

After blocking, the support is suspended in 3 ml of TBS and an appropriate dilution (generally 1:50-1:500) of unlabeled anti-EGF antibody is provided. Binding is allowed to occur for 1-2 hrs., at room temperature on a shaker, and, subsequently, the support is washed in TBS and air-dried. Next, 3 ml of a ferrofluid solution (1:1 v/v) is added to the support and is allowed to interact with the proteins on the support for 5-10 minutes. After a sufficient time, the unbound ferrofluid is removed from the support by successive washes of TBS. The support bound with ferrofluid is air-dried and is passed before a GMR sensor to detect the magnetic signal present. Because the protein attached to an antibody will generate a greater magnetic signal than unbound protein on the support, a determination of the presence and location of the target protein on the support can be made.

Once the magnetic signal on the support has been measured, the probe is stripped from the support, by conventional techniques, and the support is reprobed with the control antibody. Alternatively, a duplicate SDS/PAGE gel can be run on total proteins isolated from the submaxillary glands from mice and the proteins can be transferred to a membrane and probed with the control antibody. The results from this example will demonstrate that conventional techniques in immunoblotting can be readily adapted for use with embodiments of the present invention.

EXAMPLE 11

The invention also provides methods and systems to detect several target proteins on a support by using multiple ferrofluid-labeled probes. In this example, the invention detects several target proteins in the same reaction by using multiple ferrofluid-labeled antibody probes. The probes in this example include a first antibody, the anti-EGF antibody described above, and a second antibody anti-Golgi 58K protein (Sigma G2404). The anti-golgi 58K protein recognizes an epitope on the microtubule-binding peripheral Golgi membrane 58K protein. (Bloom and Brashear *J. Biol. Chem.,* 264:16083 (1989)). The first target protein is EGF and the second target protein is the 58K protein. The first antibody is labeled with a first magnetic label (e.g., a first ferrofluid) and the second antibody is labeled with a second magnetic label (e.g., a second ferrofluid) such that the first and the second magnetic labels are different and exhibit different magnetic signals. Labeling is accomplished, as described above.

Total protein from mouse submaxillary glands is isolated, according to conventional techniques, and is separated on a 15% SDS/PAGE (5-20 ug per well). As in the example above, after gel electrophoresis, the separated proteins are transferred to a membrane by electroblotting and are immobilized to the support by heating the membrane under vacuum. Subsequently, the membrane is blocked in a solution of 5% w/v BSA and TBS (Sigma) for 2 hrs. at room temperature). Other blocking agents and/or a non-magnetic colloids may be added.

Once blocking is complete, the support is suspended in 3 ml of TBS and an appropriate dilution of the magnetically-labeled probes (generally 1:50-1:500 for the first probe and 1:5000 for the second probe) is added. Binding is allowed to take place for 1-2 hrs. at room temperature on a shaker and, subsequently, the membrane is washed in TBS and allowed to air dry.

In this embodiment detection is accomplished with a vibrating sample magnetometer or other suitable instrument as described above. Because the first and second probe are labeled with different magnetic labels, having unique magnetic signals, the detection of one or both of the antibody probes can be accomplished in the same reaction. The results of this example demonstrate that several proteins present in a biological sample disposed on a support can be detected in the same reaction by using different antibody probes having unique magnetic labels.

EXAMPLE 12

The invention also rapidly detects the presence of a target protein molecule in a solution by using a probe attached to a colored support. In this example, the invention provide methods and systems to rapidly detect a target protein in a solution by using a ferrofluid-labeled probe. Accordingly, an antibody specific for a target biomolecule is attached to a colored support. In one embodiment, the probe antibody is the anti-EGF antibody, described above. The probe antibody can be coupled to a colored bead by conventional techniques (e.g., a Protein A bead or a Streptavidin bead coupled to a biotinylated anti-mouse IgG antibody). The immobilized probe antibody is then placed in a solution containing total protein isolated from mouse submaxillary glands. Binding is allowed to occur for a period of time and the colored beads are washed in TBS (Sigma). After washing, the beads are resuspended in TBS and a thin magnet is placed near the side of the vessel. The presence of EGF in the solution is indicated by the aggregation of colored beads near the magnet. These results demonstrate a rapid method to determine the presence of a specific protein in a solution.

EXAMPLE 13

The invention includes methods and systems that perform competitive binding studies. In this example, the invention provides methods and systems to determine competitive binding of two molecules, each having a unique magnetic label. Competitive binding or competitive inhibition studies are useful for the determination-of the avidity of biomolecules which interact with a target biomolecule. In one embodiment, the target biomolecule is a nucleic acid sequence and the competitive binding of a first nucleic acid sequence (probe 1) which has 100% complementarity to the target biomolecule and a second nucleic acid sequence (probe 2) which has only 80% complementarity to the target biomolecule is studied by labeling probe 1 with a ferrofluid that is different than the ferrofluid used to label probe 2.

The target biomolecule and the two ferrofluid-labeled probes are brought in contact with each other in a hybridization solution and hybridization is allowed to take place for 16 hrs. at a moderately stringent temperature (e.g., 37° C.). After hybridization, the support is washed in a suitable wash buffer, air-dried, and the magnetic characteristics of the bound magnetic probes are measured. The presence of the first and/or second magnetic signal on the support, representative of the presence of the first and/or second probe hybridized to the target biomolecule, can be determined over time. By conducting serial hybridizations, for example, and stopping each at various time points, the kinetics of competitive binding can be efficiently evaluated. Because the two magnetic labels attached to the two probes have unique magnetic signals, their presence on the support can be determined in the same reaction.

This embodiment can also be used to study competitive binding of protein ligands, such as antibodies, to a shared epitope on a target biomolecule. As detailed above, the two ligands are magnetically labeled with two different magnetic markers and immunoblotting with the two magnetically-labeled probes is carried out. The presence of the magnetic labels and, thus, the ligands, on the support is evaluated. As above, the detection of one or both of the magnetic labels can be accomplished in the same reaction and the binding kinetics can be studied over time. The use of multiple probes which bind to the same target biomolecule can also be accomplished by using the approaches detailed above so long as each probe has a different magnetic label having a unique magnetic signal. Results from these examples demonstrate that conventional competitive binding assays can be adapted to and enhanced by embodiments of the present invention. More specifically, the use of this embodiment will allow for a dynamic determination of competitive binding in several biochemical interactions including ligand-receptor, antibody-antigen, and nucleic acid hybridization assays.

Preferred embodiments of the present invention have been disclosed. A person of ordinary skill in the art would realize, however, that certain modifications would come within the teachings of this invention, and the following claims should be studied to determine the true scope and content of the invention. In addition, the methods and structures of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive. All references cited herein are hereby expressly incorporated by reference.

What is claimed is:

1. A method assaying molecules in a sample comprising the steps of: providing a sample that contains one or more target molecules or molecular complexes; contacting said target with one or more probes under conditions which permit the formation of a target-probe complex, wherein the probe comprises one or more magnetic labels; subjecting said target-probe complex to an applied magnetic field so as to induce magnetization; and generating a signal with a giant magnetoresistive ratio magnetic sensor in response to the applied magnetic field so as to identify the presence of the target-probe complex in a sample.

2. The method of claim 1, further comprising: providing a signal processing means that generates readable output from said signal.

3. The method of claim 1 wherein said one or more target molecules or molecular complexes are disposed on a support; and wherein said signal generating comprises: moving the support and the sensor in relation to each other in one or more directions so as to identify the presence of the target-probe complex in a sample.

4. The method of claim 1, further comprising: subjecting said target-probe complex to one or more of a plurality of applied magnetic fields having different intensities.

5. The method of claim 1, further comprising: subjecting said target-probe complex to one or more of a plurality of applied magnetic fields having different directions.

6. The method of claim 1, further comprising: contacting the one or more target molecules or molecular complexes with a non-magnetic colloid so as to block the magnetic signal from the reduce non-specific binding of the one or more probes to the target molecules or molecular complexes.

7. The method of claim 1, further comprising: joining the one or more probes to one or more colored beads, fluorescent beads, or fluorescent cells.

8. The method of claim 1, further comprising the step of detecting the presence of said target-probe complex by visual, electronic or optical means.

9. A method of assaying molecules in a sample comprising the steps of: providing a sample that contains one or more target molecules or molecular complexes; contacting said target with one or more probes under conditions which permit the formation of a target-probe complex, wherein the probe comprises one or more magnetic labels; subjecting said target-probe complex to an applied magnetic field so as to induce magnetization of the target-probe complex; and scanning in a raster-scan motion with a magnetic sensor a magnetic signal of said target-probe complex induced by said applied magnetic field so as to identify any of the presence, location, orientation and quantity of the target probe complex, and thus also one or more target-probe complexes.

10. The method of claim 9, wherein the determining of the magnetic signal of said target-probe complex induced by said applied magnetic field also determines a time response, called magnetic swing time, of the target-probe complex.

11. The method of claim 9, wherein the determining of the magnetic signal of said target-probe complex induced by said applied magnetic field also determines the spatial orientation of the target-probe complex.

12. The method of claim 9, wherein the determining of the magnetic signal of said target-probe complex induced by said applied magnetic field determines a hysteresis loop that is solvable for any of (1) saturation magnetization, (2) remnant magnetization, (3) coercive force and (4) magnetic magnitude.

13. The method of claim 1 further comprising: determining from the generated signal a time response, called magnetic swing time, of the target-probe complex.

14. The method of claim 1 further comprising: determining from the generated signal the spatial orientation of the target-probe complex.

15. The method of claim 1 further comprising: determining from the generated magnetic signal a hysteresis loop that is solvable for any of (1) saturation magnetization, (2) remnant magnetization, (3) coercive force and (4) magnetic magnitude.

16. A method assaying molecules in a sample comprising the steps of: contacting one or more target molecules or molecular complexes disposed on a support with a non-magnetic colloid so as to block or reduce a magnetic signal from the non-specific binding of the magnetic colloid to the target molecules or molecular complexes; contacting said target with one or more probes under conditions which permit the formation of a target-probe complex; contacting the one or more probe molecules or molecular complexes with a magnetic colloid; subjecting said target-probe complex to an applied magnetic field so as to induce magnetization; and generating a signal with a giant magnetoresistive ratio magnetic sensor in response to the applied magnetic field so as to identify the presence of the target-probe complex in a sample.

17. The method of claim 16, further comprising: providing a signal processing means that generates readable output from said signal.

18. The method of claim 16 wherein said one or more target molecules or molecular complexes are disposed on a support; and wherein said generating signal comprises a step: moving the support and the sensor in relation to each other in one or more directions so as to identify the presence of the target-probe complex in a sample.

19. The method of claim 16, further comprising: subjecting said target-probe complex to one or more of a plurality of applied magnetic fields having different intensities.

20. The method of claim 16, further comprising: subjecting said target-probe complex to one or more of a plurality of applied magnetic fields having different directions.

21. The method of claim 16, further comprising: joining the one or more probes to one or more colored beads, fluorescent beads, or cells which produce fluorescent signal.

22. The method of claim 16, further comprising the step of detecting the presence of said target-probe complex by visual, electronic or optical means.

23. A method assaying molecules in a sample comprising the steps of: binding one or more probe molecules or molecular complexes to a colored bead a fluorescent bead, or a cell which produces fluorescent signal; contacting one or more target molecules or molecular complexes with a magnetic colloid; contacting said target with said one or more probes in a tube under conditions which permit the formation of a target-probe complex; subjecting said target-probe complex to an applied magnetic field so as to induce magnetization and concentration of the target colored bead-magnetic probe complex on the wall of the tube; and viewing the color produced by the concentrated target colored bead-magnetic probe complex so as to identify the presence of the target-probe complex in a sample.

24. The method of claim 23, further comprising: binding one or more probe molecules to one or more different colored beads, different fluorescent beads, or cells which different fluorescent signal.

25. The method of claim 23, further comprising a step of detecting the presence of said target colored bead-magnetic probe complex by visual, electronic or optical means.

26. The method of claim 23, further comprising a step of concentration of the target colored bead-magnetic probe complex on the wall of a vessel, a glass tube, a plastic tube, a capillarity tube or a channel.

27. The method of claim 1, wherein said target molecule or molecular complex is disposed on a support.

28. The method of claim 1, wherein said target molecule or molecular complex is disposed on the support in an array.

29. The method of claim 1, wherein said sample is identified by an addressable giant magnetoresistive ratio magnetic sensor array.

30. The method of claim 1, wherein said one or more probes are disposed on a support.

31. The method of claim 30, wherein said one or more probes are disposed on the support in an array.

32. The method of claim 31, wherein said array is an addressable array.

33. The method of claim 1 wherein the contacting of said target is with one or more probes containing a ferrofluid as the magnetic label.

* * * * *

UNITED STATES PATENT AND TRADEMARK OFFICE
CERTIFICATE OF CORRECTION

PATENT NO. : 7,504,262 B2 Page 1 of 1
APPLICATION NO. : 11/361828
DATED : March 17, 2009
INVENTOR(S) : John S. Fox It is certified that error appears in the above-identified patent and that said Letters Patent is hereby corrected as shown below:

Title Page item 76
Please change Inventor address to

Inventor: John Fox, 684 Poinsettia Park
South, Encinitas, CA (US) 92024

Signed and Sealed this

Twenty-third Day of February, 2010

David J. Kappos
*Director of the United States Patent and Trademark Office*